United States Patent [19]

Kuelzow et al.

[11] Patent Number: 4,497,773
[45] Date of Patent: Feb. 5, 1985

[54] PROCESS AND APPARATUS FOR SHORTENING THE DRYING STAGE OF A STEAM STERILIZATION CYCLE

[75] Inventors: Christopher J. Kuelzow, Little Silver; Edward M. Kackos; Francis J. Murray, both of Belmar, all of N.J.

[73] Assignee: Vernitron Corporation, Lake Success, N.Y.

[21] Appl. No.: 529,494

[22] Filed: Sep. 6, 1983

Related U.S. Application Data

[63] Continuation-in-part of Ser. No. 241,247, Mar. 3, 1981, abandoned.

[51] Int. Cl.$^3$ ............................................. A61L 2/00
[52] U.S. Cl. ................................... 422/26; 422/297
[58] Field of Search .............. 422/25, 26, 27, 295, 422/297; 165/2

[56] References Cited

U.S. PATENT DOCUMENTS

| | | | |
|---|---|---|---|
| 3,088,180 | 5/1963 | Lauterbach | 422/25 |
| 3,687,612 | 8/1972 | Ernst | 422/27 |
| 3,861,872 | 1/1975 | MacFarlane | 422/25 |
| 4,164,538 | 8/1979 | Young et al. | 422/26 |
| 4,238,447 | 12/1980 | Wolff | 422/26 |
| 4,263,258 | 4/1981 | Kalasek | 422/26 X |

FOREIGN PATENT DOCUMENTS

| | | | |
|---|---|---|---|
| 1930908 | 12/1970 | Fed. Rep. of Germany | 422/295 |
| 1792770 | 2/1975 | Fed. Rep. of Germany | 422/26 |
| 583064 | 12/1976 | Switzerland | 422/26 |

Primary Examiner—Barry S. Richman
Assistant Examiner—Brion P. Heaney
Attorney, Agent, or Firm—Edward H. Loveman

[57] ABSTRACT

A process and apparatus for improving a steam sterilization cycle by shortening the time of the drying stage of the cycle. Sterilized articles in a sterilization chamber surrounded by a steam jacket chamber, are enveloped in water vapor which is quickly cooled and condensed by draining steam from the jacket. In addition, a heat exchanger comprising pipe coils mounted within the sterilization chamber completely below the articles to be sterilized with a cold coolant circulated therethrough may be used to further cool and condense the water vapor in the sterilization chamber, from which water and water vapor are quickly drawn off by an applied vacuum. The process involves the simultaneous steps of: withdrawing steam from the steam jacket to cool the walls of the sterilizing chamber; removing water and water vapor by vacuum from the sterilizing chamber; and circulating cold coolant in the heat exchanger.

3 Claims, 3 Drawing Figures

PROCESS AND APPARATUS FOR SHORTENING THE DRYING STAGE OF A STEAM STERILIZATION CYCLE

This application is a continuation-in-part of my prior copending application Ser. No. 241,247, filed Mar. 3, 1981, now abandoned.

This invention relates to a steam sterilization process and apparatus, and more particularly to a method and means for effecting rapid cooling of a sterilization chamber during a drying stage of a sterilization cycle therein, to shorten the time of the sterilization cycle.

When sterilizer apparatus is in heavy duty use such as in hospitals where large numbers of wrap fabric loads are to be steam sterilized, it is imperative that the time of the sterilization cycle be minimized to maximize the number of loads sterilized in a given time.

It has been proposed heretofore to modify the cooling step by spraying a cooling liquid into the chamber. Such a method is described in U.S. Pat. No. 3,897,818, and is used with closed containers of food and the like heat processed in a steam chamber. Such a method cannot be used with sterilizers where wrap articles such as surgical gowns, bed linens, nurses uniforms, and the like are steam sterilized because the spraying of cool water on the sterilized articles retards the drying stage and lengthens the sterilization cycle.

It has also been proposed to roughen the interior walls of the steam sterilization chamber as described in U.S. Pat. No. 3,861,872 to prevent formation of water droplets which could fall on the sterilized load, and thus, reduce the length of time required to dry the sterilized load. This method is a passive one, and does not appreciably reduce the drying time.

The present invention involves and takes advantage of the discovery that the drying time of a steam sterilized load may be shortened by rapidly cooling the chamber at the start of the drying stage, so that the fog of steam vapor in the chamber, condenses as water, away from the sterilized articles. As a result the drying time is shortened. As a further advantage it has been discovered that the fabric and other articles in the load are appreciably drier at the end of a predetermined drying time, than in a sterilization cycle conducted without cooling of the chamber and chamber walls during the drying stage.

It is therefore a principal object of the present invention to provide an improved sterilization cycle in which rapid cooling is effected during a drying stage to shorten the drying time.

A further object of the present invention is to provide a steam sterilization chamber with a heat exchanger inside the chamber to effect rapid cooling of the chamber at the start of a drying stage.

Another object of the present invention, is to provide an improved steam sterilization cycle and apparatus in which steam externally surrounding a sterilization chamber is drawn off at the end of the sterilization stage and start of the drying stage, while the chamber and walls are rapidly cooled by heat exchanging.

These and other objects and many of the attendant advantages of this invention will be readily appreciated as the same becomes better understood by reference to the following detailed description when considered in connection with the accompanying drawings in which.

Figure 1:
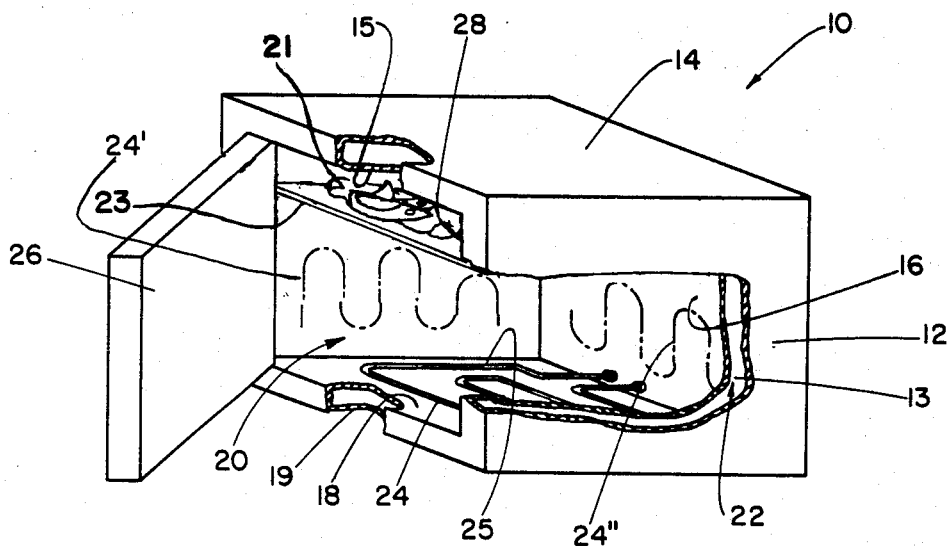
FIG. 1 is a perspective view of a steam sterilization apparatus embodying the invention, parts being broken away.
Figure 2:
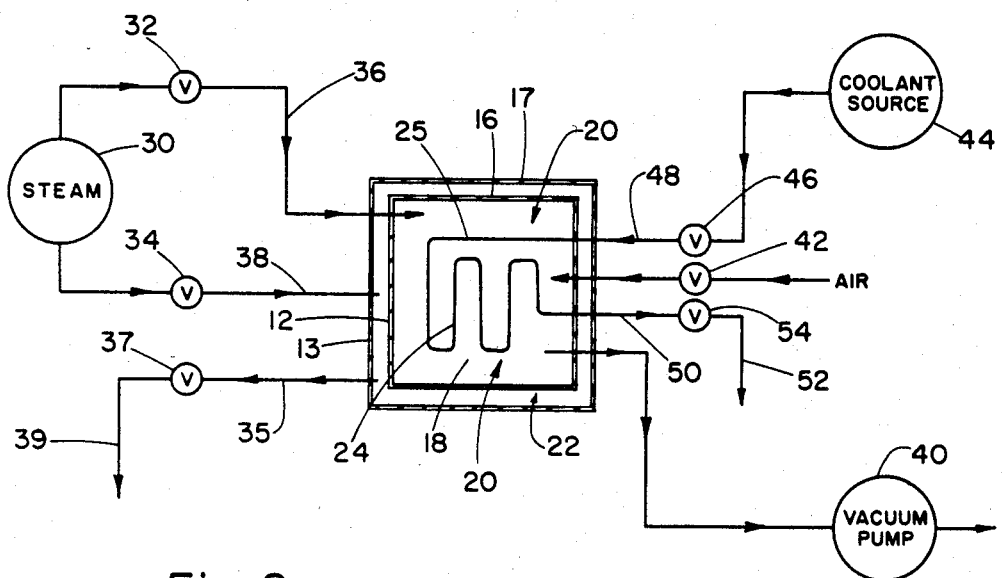
FIG. 2 is a diagram of components of sterilization apparatus embodying the invention, shown schematically.

Referring now to the drawings, wherein like reference characters designate like or corresponding parts throughout, there is illustrated in FIGS. 1 and 2, a sterilization apparatus generally designated as reference numeral 10 comprising a pair of spaced vertical side walls 12, 13, a pair of spaced top walls 14, 15, a pair of spaced back walls 16, 17, and a pair of spaced bottom walls 18, 19 defining an interior sterilizing chamber 20 and a closed steam jacket chamber 22 externally of and surrounding the chamber 20. On the floor 18, in the chamber 20 is a heat exchanger comprised of a plurality of coils 24 of a pipe 25 through which a coolant such as cold water may be circulated to cool the chamber 20. A door 26 at an open end 28 of the chamber 20 may be closed and sealed. The chamber 20 is loaded with articles 21 to be sterilized by inserting them through the open end 28 of the chamber 20, and placing them on a shelf 23 above the coils 24. A source 30 of steam is connected via a pair of valves 32, 34 and a pair of steam input pipes 36, 38 which open into the sterilizing chamber 20 and jacket chamber 22 respectively. Steam and water are drawn from the jacket 22 via a pipe 35, and a valve 37 to a drain 39. A vacuum pump 40 has its inlet open to the sterilizing chamber 20 for drawing off water and water vapor. Atmospheric air may be admitted into the sterilizing chamber 20 via a valve 42 to relieve any vacuum therein. A supply or source 44 of a coolant is connected via a valve 46 and an inlet pipe 48 to a pipe 25 on the floor of the sterilizing chamber 20. An outlet pipe 50 is connected to the pipe 25 and opens into a drain 52 via a valve 54.

Figure 3:
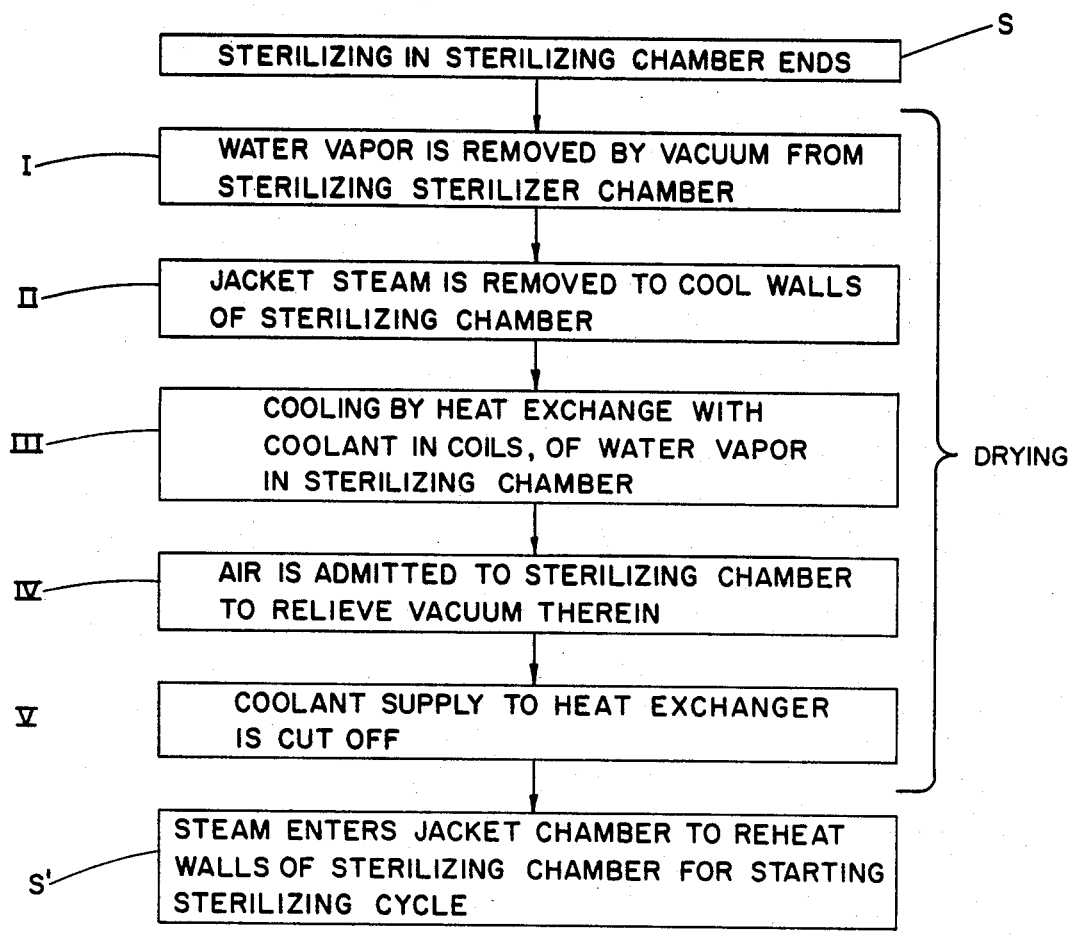
FIG. 3 is a flow diagram of several stages in a sterilization cycle including the improved drying stage, according to the invention.

FIG. 3 shows steps in a drying stage D of a sterilization cycle which starts just after sterilization stage S is completed. In step I, the source 30 of steam is cut off from the chambers 20 and 22 by closing the valves 32 and 34. Water vapor is removed from the sterilizer chamber 20 by turning on the vacuum pump 40; see FIG. 2. In step II, the valve 37 is opened and steam passes from the jacket chamber 22 via the drain pipe 35. Step II is preferably done at the same time as Step I. This causes immediate cooling of the chamber walls 12–19. In Step III, the valve 46 is opened and a cold coolant flows from the source 44 through the pipes 48 and 25 to effect further cooling and condensing of vapor in the sterilizing chamber 20 by heat exchange with the coolant. The valve 54 is opened so that the coolant flows out of the heat exchanger 21 via the drain pipes 50 and 52. The coolant never contacts sterilized articles in the sterilizing chamber 20. In step IV, air is admitted into the sterilizing chamber 20 via the valve 42 which is opened to relieve the vacuum in the chamber 20. The valve 46 is closed to cut off admission of coolant to the heat exchanger 21, in Step V. This completes the cooling and drying stage D. The door 26 may now be opened to remove the sterilized load. Steam can then be admitted to the jacket chamber 22 again, by opening the valve 34 to reheat the chamber walls at the start of another sterilization cycle S.

The basic features of the improved drying stage D which distinguish it from those conventionally used are the removal of steam from the jacket space 22 and passage of cold coolant through the heat exchanger coils to effect immediate cooling of the walls of chamber 20 and vapor in the chamber 20. Although the coils 24 of the heat exchanger 21 are shown on the floor 18, they can if desired also be mounted at the vertical side and the back walls 13 and 16 as indicated by dot and dash lines representing further alternate or optional heat exchanger coils 24' and/or 24" inside the sterilizer chamber 20. Water will condense on these coils and will be drained by the pump 40. The coils 24' and/or 24" must be located below the articles 21 being sterilized to insure that the steam which condenses to water on the sterilizer chamber walls does not contaminate the articles 21.

It has been found that drying time may be reduced by several minutes when accelerated cooling is performed as described herein, so that more loads may be sterilized in the sterilizer apparatus in a given working time. It has also been found that by use of the present invention, the articles coming out of the sterilizer at the end of the drying stage are appreciably drier than heretofore experienced with conventional sterilizers and sterilizer cycles.

It should be understood that the foregoing relates to only a preferred embodiment of the invention which has been described by way of example only and that it is intended to cover all changes and modifications of the examples of the invention, herein chosen for the purpose of the disclosure, which do not constitute departures from the spirit and scope of the invention.

What is claimed is:

1. A process in a sterilization cycle for reducing the drying time of steam sterilized wrap articles enveloped by water vapor in a sterilizing chamber having walls surrounded by a jacket chamber containing steam, the wrap articles being supported and spaced from the chamber floor, comprising the simultaneous steps of:

withdrawing steam from said jacket chamber to cool said walls of said sterilizing chamber;

removing water and water vapor by vacuum from said sterilizing chamber; and circulating cold coolant in a heat exchanger located inside said sterilizing chamber completely below the wrap articles therein, so that heat exchange takes place in said sterilizer and said coolant condenses said water vapor to water in said sterilizing chamber below and out of direct contact with the wrap articles and in the vicinity of said heat exchanger thereby minimizing the time period required to dry said wrap articles.

2. A process as defined in claim 1, comprising the further steps of withdrawing by vacuum from said sterilizing chamber water obtained by condensation of said water vapor, and then admitting air to said sterilizing chamber to relieve the vacuum therein.

3. A process as defined in claim 2, comprising the further steps of cutting off supply of said coolant to said heat exchanger, and admitting steam to said jacket chamber to start a new sterilization cycle.

* * * * *